United States Patent

Jaeggi et al.

[11] 4,140,789
[45] Feb. 20, 1979

[54] ETHERIFIED HYDROXY-BENZODIHETEROCYCLIC COMPOUNDS

[75] Inventors: Knut A. Jaeggi, Basel; Franz Ostermayer, Riehen; Herbert Schröter, Fullinsdorf, all of Switzerland

[73] Assignee: Ciba-Geigy Corporation, Ardsley, N.Y.

[21] Appl. No.: 751,233

[22] Filed: Dec. 16, 1976

[30] Foreign Application Priority Data

Jan. 8, 1976 [CH] Switzerland .......................... 161/76

[51] Int. Cl.² .................. A61K 31/535; C07D 265/18; C07D 265/28
[52] U.S. Cl. .............................. 424/248.55; 544/285; 544/286; 544/354; 424/248.56; 424/251; 424/257; 424/269; 424/272; 424/273 B; 544/92; 544/105; 548/305; 260/307 C; 260/345.7 R; 260/465 E; 260/348.45; 260/348.25; 260/570.5 P; 260/570.6; 560/142; 568/587; 560/27; 560/29; 560/254
[58] Field of Search .............................. 544/92, 105; 424/248.55, 248.56

[56] References Cited

U.S. PATENT DOCUMENTS

| | | | |
|---|---|---|---|
| 3,686,176 | 8/1972 | Stuart et al. | 260/248.56 X |
| 3,763,153 | 10/1973 | Krapcho et al. | 260/248.56 X |
| 3,931,177 | 1/1976 | Coates et al. | 260/250 A |

OTHER PUBLICATIONS

Nakagawa et al., J. Med. Chem., vol. 17, pp. 529–533 (1974).

*Primary Examiner*—John D. Randolph
*Attorney, Agent, or Firm*—John J. Maitner

[57] ABSTRACT

A compound of the formula

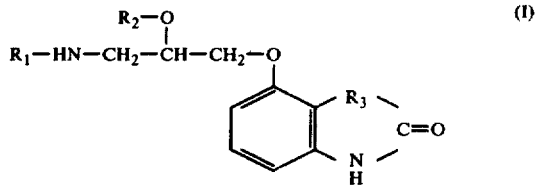

(I)

in which $R_1$ denotes optionally substituted lower akyl which is optionally branched at the linking carbon atom, $R_2$ represents hydrogen or lower alkanoyl and $R_3$ is a group of the formula $-R_3{}^a-(R_3{}^b)_n-$ (Ia), in which $R_3{}^1$ represents the radical of the formula $-N(R_4)-$ or $-O-$ and $R_4$ represents hydrogen or lower alkyl, $R_3{}^b$ denotes the radical of the formula $-CH_2-$ or, if $R_3{}^a$ represents $-N(R_4)-$, denotes the radical of the formula $-C(=O)-$ and n represents nought or 1, and a group of the formula Ia, in which n represents 1, can be linked to the carbonyl group of the carbamoyl grouping either via the group $R_3{}^a$ or the group $R_3{}^b$, or acid addition salts thereof, which can be used pharmaceutically can be used as beta-receptor blocking agents for the treatment of disorders in the cardiac rhythm and coronary heart diseases. These compounds also possess a cardio-stimulating action; some of them also display alpha-receptor-blocking properties.

9 Claims, No Drawings

ETHERIFIED HYDROXY-BENZODIHETEROCYCLIC COMPOUNDS

The present invention relates to etherified hydroxybenzodiheterocyclic compounds, especially compounds of the formula

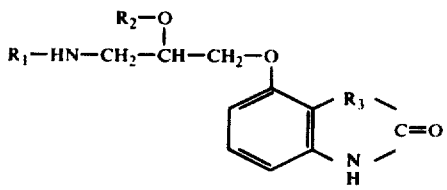

(I)

in which $R_1$ denotes optionally substituted lower alkyl which is optionally branched at the linking carbon atoms, $R_2$ represents hydrogen or lower alkanoyl and $R_3$ is a group of the formula $-R_3{}^a-(R_3{}^b)_n-$ (Ia), in which $R_3{}^a$ represents the radical of the formula $-N(R_4)-$ or $-O-$ and $R_4$ represents hydrogen or lower alkyl, $R_3{}^b$ denotes the radical of the formula $-CH_2-$ or, if $R_3{}^a$ represents $-N(R_4)-$, denotes the radical of the formula $-C(=O)-$ and n represents nought or 1, and a group of the formula Ia, in which n represents 1, can be linked to the carbonyl group of the carbamoyl grouping either via the group $R_3{}^a$ or the group $R_3{}^b$, or salts thereof and processes for the manufacture of these compounds and also pharmaceutical formulations containing compounds of the formula I, or salts thereof which can be used pharmaceutically, and the use of these compounds, preferably in the form of pharmaceutical formulations.

Lower alkyl $R_1$ preferably has from 3 to 5 carbon atoms and is, above all, isopropyl or tert.-butyl but can also be sec.-butyl or 2-methyl-2-butyl.

Substituents of lower alkyl $R_1$ are, for example, aryl or aryloxy, in which aryl denotes an optionally substituted aromatic radical, above all optionally substituted phenyl. Substituted phenyl contains, for example, lower alkyl, hydroxyl, lower alkoxy, methylenedioxy, halogen and/or optionally N-substituted carbamoyl as substituents and 1 to 3 of these substituents can be present and these can either be identical or different.

Substituted lower alkyl $R_1$ is therefore aryl-lower alkyl or aryloxy-lower alkyl which is optionally branched at the linking carbon atom, and especially phenyl-lower alkyl or phenoxy-lower alkyl which is optionally substituted in the phenyl radical, for example as indicated, and optionally branched at the linking carbon atom, such as corresponding 1-phenyl- or 1-phenoxy-2-propyl or 4-phenyl- or 4-phenoxy-2-butyl, but in addition also 2-phenyl-ethyl, which are optionally substituted in the phenyl radical, for example as indicated, and in which a substituted phenyl radical can be substituted, for example, by lower alkyl, hydroxyl, lower alkoxy, methylenedioxy, halogen and/or optionally N-substituted carbamoyl.

In the context of the present description, radicals or compounds designated as "lower" contain, unless otherwise defined, preferably up to 7 and above all up to 4 carbon atoms.

Unless specifically defined as above for $R_1$ lower alkyl is, for example, methyl, ethyl, n-propyl, isopropyl, n-butyl, isobutyl, sec.-butyl, tert.-butyl, n-pentyl, 1-methyl-2-butyl or neopentyl.

Lower alkoxy is, for example, methoxy, ethoxy, n-propoxy, n-butoxy or isobutoxy.

Halogen is, above all, halogen with an atomic number of up to 35, that is to say fluorine or bromine and especially chlorine.

Carbamoyl is preferably N-unsubstituted but can also be, for example, N-lower alkyl-carbamoyl or N,N-di-lower alkyl-carbamoyl, for example N-methylcarbamoyl, N-ethylcarbamoyl or N,N-dimethylcarbamoyl.

Lower alkanoyl is, for example, acetyl or propionyl but above all pivaloyl.

Salts of compounds of the formula I are above all acid addition salts and especially non-toxic acid addition salts, which can be used pharmaceutically, with suitable inorganic acids, such as hydrochloric acid, hydrobromic acid, sulphuric acid or phosphoric acid, or with suitable organic aliphatic, cycloaliphatic, aromatic, araliphatic or heterocyclic carboxylic acids or sulphonic acids, such as formic acid, acetic acid, propionic acid, succinic acid, glycolic acid, lactic acid, malic acid, tartaric acid, citric acid, ascorbic acid, maleic acid, fumaric acid, pyruvic acid, benzoic acid, anthranilic acid, 4-hydroxybenzoic acid, salicylic acid, phenylacetic acid, embonic acid, methanesulphonic acid, ethanesulphonic acid, hydroxyethanesulphonic acid, ethylenesulphonic acid, 4-chlorobenzenesulphonic acid, toluenesulphonic acid, naphthalenesulphonic acid, sulphanilic acid or cyclohexylaminesulphonic acid.

Because of the close relationships between the new compounds in the free form and in the form of their salts, the free compounds, and the salts, are, where appropriate, also to be understood to include the corresponding salts or free compounds respectively, in respect of general sense and intended use.

The new compounds can be in the form of racemates or of antipodes.

The new compounds display valuable pharmacological properties, in particular strong and long-lasting beta-receptor-blocking actions, which can be demonstrated with the aid of corresponding pharmacological experiments (see, for example, Meier et al., Arzneimittelforschung, volume 20, page 1890 (1970)). Thus, in a concentration range of from about 0.001 μg/ml to about 1 μg/ml the new compounds inhibit the isoproterenol tachycardia in an isolated guinea-pig heart (according to Langendorff) and in a dosage range of from about 0.0003 mg/kg to about 0.3 mg/kg they inhibit the isoproterenol tachycardia and vasodilatation in narcotised cats on intravenous administration. The new compounds can therefore be used as beta-receptor-blocking agents, for example for the treatment of disorders in the cardiac rhythm (arrhythmia) and coronary heart diseases, such as angina pectoris, and also as hypotensive agents in the treatment of hypertension. Moreover, these compounds also possess a cardio-stimulating action, which can be demonstrated, for example, in a concentration range of from about 0.003 to about 3 μg/ml on an isolated atrium of a guinea-pig as an increase in the heart rate and in the myocardial contractility. This mode of action can also be demonstrated in a dosage range of from about 0.0003 to about 0.3 mg/kg, administered intravenously, on narcotised cats in the form of an increase in the heart rate and in the maximum rate of the increase in pressure (dP/dt) in the left ventricle. Compounds having such a cardio-stimulating action therefore have a less adverse effect on the function of the heart than substances which do not possess these additional properties.

Some of these compounds also display alpha-receptor-blocking properties which, for example, manifest themselves, in a concentration range of from about 0.03 to about 3 μg/ml, as an inhibition of a noradrenalin-induced vasoconstriction in a rat mesenteric bed which is perfused in isolation. A hypotensive action, for example, can be promoted by this component of the action.

The invention relates above all to compounds of the formula I in which $R_1$ denotes lower alkyl with 3–5 carbon atoms which is optionally branched at the linking carbon atom and can be substituted, on a carbon atom other than the linking carbon atom, by phenyl which optionally contains hydroxyl, as well as lower alkyl, for example methyl, lower alkoxy, for example methoxy, methylenedioxy or halogen, for example chlorine, or by phenoxy which optionally contains carbamoyl, $R_2$ represents hydrogen and $R_3$ represents the group of the formula Ia in which $R_3{}^a$ denotes the radical of the formula —NH— or —O— as well as —NR$_4$—, in which $R_4$ represents lower alkyl, and $R_3{}^b$ and n have the abovementioned meanings and a group of the formula Ia, in which n represents 1, can be linked to the carbonyl grouping either via the radical $R_3{}^a$ or the radical $R_3{}^b$, or salts, especially acid addition salts which can be used pharmaceutically, of such compounds.

The invention relates in particular to compounds of the formula I in which $R_1$ denotes lower alkyl with 3–5 carbon atoms which is optionally branched at the linking carbon atom or denotes 2-phenyl-lower alkyl, in which lower alkyl contains up to 3 carbon atoms, which is optionally substituted in the phenyl part by lower alkoxy, for example methoxy or methylenedioxy, $R_2$ represents hydrogen and $R_3$ denotes the group of the formula Ia, in which $R_3{}^a$ represents the radical of the formula —O— and especially —NH—, and also —NCH$_3$—, and $R_3{}^b$ and n have the abovementioned meanings and a group of the formula Ia, in which n represents 1, can be linked to the carbonyl grouping either via the radical $R_3{}^a$ or the radical $R_3{}^b$, or salts, especially acid addition salts which can be used pharmaceutically, of such compounds.

The invention relates in particular to compounds of the formula I in which $R_1$ denotes lower alkyl with 3–5 carbon atoms which is branched at the linking carbon atom, especially isopropyl or tert.-butyl, $R_2$ represents hydrogen and $R_3$ denotes the group of the formula Ia, in which $R_3{}^a$ represents the radical of the formula —NH— and also of the formula —NCH$_3$— and n represents nought, or salts, especially acid addition salts which can be used pharmaceutically, of such compounds.

The invention relates above all to compounds of the formula I in which $R_1$ denotes 2-phenyl-lower alkyl which is optionally substituted by lower alkoxy, for example methoxy or 3,4-methylenedioxy and in which lower alkyl contains up to 3 carbon atoms, $R_2$ represents hydrogen and $R_3$ denotes the group of the formula Ia, in which $R_3{}^a$ denotes the radical of the formula —NH—, and n represents nought, or salts, especially acid addition salts which can be used pharmaceutically, of such compounds.

The invention relates in particular to compounds of the formula I in which $R_1$ denotes lower alkyl with 3–5 carbon atoms which is branched at the linking carbon atom, especially isopropyl or tert.-butyl, and $R_3$ represents the group Ia, in which $R_3{}^a$ denotes the radical of the formula —O— and $R_3{}^b$ represents the radical of the formula —CH$_2$—, and n represents nought or 1, and the group of the formula Ia, in which n represents 1, can be linked to the carbonyl grouping either via the radical $R_3{}^a$ or the radical $R_3{}^b$, or salts, especially acid addition salts which can be used pharmaceutically, of such compounds.

The invention relates specifically to the compounds of the formula I described in the examples, or salts, especially acid addition salts which can be used pharmaceutically, of such compounds.

The new compounds of the present invention can be manufactured in a manner which is in itself known.

Thus, the new compounds can be obtained, for example, when a compound of the formula

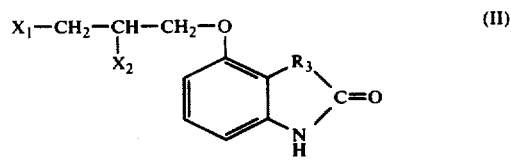

(II)

is reacted with a compound of the formula R—X$_3$ (III), in which one of the groups X$_1$ and X$_3$ represents a reactive esterified hydroxyl group and the other represents a primary amino group and X$_2$ represents hydroxyl or lower alkanoyloxy, or in which X$_1$ and X$_2$ together denote the epoxy group and X$_3$ represents a primary amino group, and, if desired, a resulting compound is converted into another compound of the formula I and/or, if desired, a resulting free compound is converted into a salt or a resulting salt is converted into a free compound and/or, if desired, a resulting racemate is resolved into the antipodes.

A reactive esterified hydroxyl group X$_1$ or X$_3$ is a hydroxyl group esterified by a strong acid, especially a strong inorganic acid, such as a hydrogen halide acid, especially hydrochloric acid, hydrobromic acid or hydriodic acid, or sulphuric acid, or a strong organic acid, especially a strong organic sulphonic acid, such as an aliphatic or aromatic sulphonic acid, for example methanesulphonic acid, 4-methylphenylsulphonic acid or 4-bromophenylsulphonic acid, and represents, above all, halogen, for example chlorine, bromine or iodine, or sulphonyloxy with aliphatic or aromatic substituents, for example methylsulphonyloxy or 4-methylphenylsulphonyloxy.

The above reaction is carried out in a manner which is in itself known and, especially when using a starting material containing a reactive esterified hydroxyl group, is advantageously carried out in the presence of a basic agent, such as an inorganic base, for example an alkali metal carbonate or hydroxide or alkaline earth metal carbonate or hydroxide, or an organic basic agent, such as an alkali metal lower alkanolate, and/or of an excess of the basic reactant and usually in the presence of a solvent or solvent mixture and, if necessary, with cooling or warming, for example in a temperature range of from about −20° to about +150°, in an open or closed vessel and/or in an inert gas atmosphere, for example in a nitrogen atmosphere.

The starting materials of the formula II can be manufactured in a manner which is in itself known, for example by converting the phenolic hydroxyl group in a compound which corresponds to the starting material of the formula II and has a free phenolic hydroxyl group in place of an etherified hydroxyl group, or the phenolic hydroxyl group in a precursor thereof, which may be monocyclic, into the allyloxy group and converting the latter into the desired group of the formula $X_1$—$CH_2$—$CH(X_2)$—$CH_2$—O— (IIa). Thus, it is possible, for example, to convert the phenolic hydroxyl group in a di-lower alkyl 3-hydroxy-phthalate into an allyloxy group by treatment with an allyl halide, for example allyl bromide, in the presence of a suitable base, such as an alkali metal carbonate, for example potassium carbonate, to liberate 3-allyloxy-phthalic acid from the ester by hydrolysis, for example by treatment with an alkali metal hydroxide, and to convert the acid into the corresponding anhydride, for example by treatment with acetic anhydride. Modified Curtius degradation of 3-allyloxy-phthalic anhydride, which is thus obtainable, for example by treatment with a suitable azide compound, such as a tri-lower alkylsilyl azide, especially trimethylsilyl azide, gives, on subsequent hydrolysis, 4-allyloxy-benzimidazol-2-one. The allyl group is converted into the desired 2,3-epoxy-propyl group, for example by oxidation with hydrogen peroxide or a suitable inorganic or organic per-acid, for example 3-chloroperbenzoic acid; this group can be converted into a 2-hydroxy-3-(reactive hydroxyl)-propyl group by treating the corresponding compound with a suitable strong acid, such as a hydrogen halide acid, and the hydroxyl group in this group can, if desired, be converted into a lower alkanoyloxy group, for example by treatment with a suitable reactive derivative, such as an optionally mixed anhydride, of a lower alkanecarboxylic acid.

A further process for the manufacture of compounds of the formula I in which $R_1$ denotes a lower alkyl radical which is optionally substituted and contains a hydrogen atom on the linking carbon atom consists in reducing the groupings of the formula $R_0$=N— (IVa) in a compound of the formula

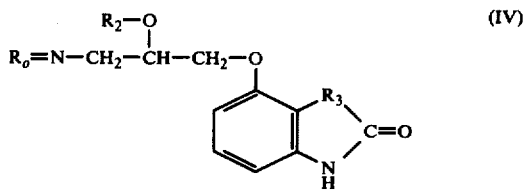

(IV)

in which $R_0$ represents the optionally substituted lower alkylidene radical which corresponds to an optionally substituted lower alkyl radical $R_1$, to the grouping of the formula $R_1$—NH— (IVb) and, if desired, carrying out the additional process steps.

The above conversion, by reduction, of a radical of the formula IVa into the desired grouping of the formula IVb can be carried out in a manner which is in itself known and suitable reducing agents which can be used are, in particular, light metal hydride reducing agents, such as alkali metal borohydrides, for example sodium borohydride, and alkali metal cyanoborohydrides, for example sodium cyanoborohydride, or boron hydrides, for example diborane, and also catalytically activated hydrogen, such as, for example, hydrogen in the presence of a heavy metal catalyst, for example Raney nickel, platinum oxide or palladium.

The above reductions are carried out in a manner which is in itself known, usually in the presence of an inert solvent and, if necessary, with cooling or warming, for example in a temperature range of from about −20° to about +150°, and/or in a closed vessel under pressure and/or in an inert gas atmosphere, for example a nitrogen atmosphere.

The starting materials of the formula IV can be obtained in a manner which is in itself known by, for example, converting the phenolic hydroxyl group in a compound which corresponds to the starting material of the formula IV and has a free phenolic hydroxyl group in place of an etherified phenolic hydroxyl group, or the phenolic hydroxyl group in a precursor thereof, which may be monocyclic, into the allyloxy group and converting the latter, via the 2,3-epoxy-propoxy group and the 3-amino-2-hydroxy-propoxy group, into the desired group of the formula $R_0$=N—$CH_2$—$CH(OR_2)$—$CH_2$—O— (IVc). Thus, a preferred starting material can be obtained, for example, by treating (2,3-epoxy-propoxy)-benzimidazol-2-one with ammonia and reacting the (3-amino-2-hydroxy-propoxy)-benzimidazol-2-one which is thus obtainable with a carbonyl compound of the formula $R_0$=O (VI), in which $R_0$ has the abovementioned meaning. At a suitable stage, the hydroxyl group can be converted into a lower alkanoyloxy group, for example by treatment with a suitable reactive derivative, such as an optionally mixed anhydride, of a lower alkanecarboxylic acid.

It is possible to effect the manufacture of the starting material of the formula IV at the same time as the conversion thereof into the desired compound of the formula I if the reaction of the amino compound with the carbonyl compound is carried out in the presence of a suitable reducing agent. Thus, for example, 4-(3-amino-2-hydroxy-propoxy)-benzimidazol-2-one can be reacted with acetone in the presence of catalytically activated hydrogen or, preferably, of a hydride reducing agent, for example sodium cyanoborohydride, and a desired compound of the formula I, in which $R_1$ represents isopropyl, is obtained direct.

The new compounds of the formula I in which $R_2$ represents hydrogen can also be obtained when $X_4$ and/or $X_5$ in a compound of the formula

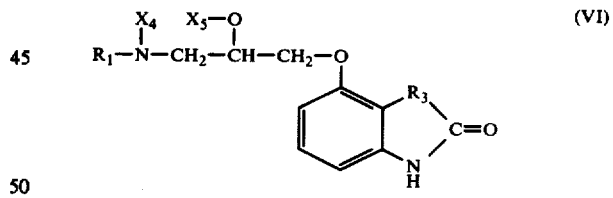

(VI)

in which at least one of the groups $X_4$ and $X_5$ denotes a group which can be replaced by hydrogen and the other represents hydrogen or represents a group which can be replaced by hydrogen, or $X_4$ and $X_5$ together represent a radical which can be split off and can be replaced by two hydrogen atoms linked to the oxygen or nitrogen atom, or in a salt thereof, are replaced by hydrogen and, if desired, the additional process steps are carried out.

The groups $X_4$ and/or $X_5$ are split off by means of solvolysis or reduction. In the abovementioned starting materials of the formula VI, $X_4$ is preferably a group which can be replaced by hydrogen whilst $X_5$ above all represents hydrogen.

A particularly suitable group $X_4$ which can be split off is, above all, an α-aryl-lower alkyl group which can be split off hydrogenolytically, such as an optionally substituted 1-phenyl-lower alkyl group, in which substituents, especially in the phenyl part, can be, for example, lower alkyl, such as methyl or tert.-butyl, hydroxyl, lower alkoxy, such as methoxy, halogen, for example chlorine or bromine, and/or nitro, and above all benzyl. A group $X_4$ can also represent a radical which can be split off by solvolysis, such as hydrolysis or acidolysis, and also a radical which can be split off by reduction, including by hydrogenolysis, especially a corresponding acyl radical, such as the acyl radical of an organic carboxylic acid, for example lower alkanoyl, such as acetyl, or aroyl, such as benzoyl, and also the acyl radical of a half-ester of carbonic acid, such as lower alkoxycarbonyl, for example methoxycarbonyl, ethoxycarbonyl or tert.-butoxycarbonyl, 2-halogeno-lower alkoxycarbonyl, for example 2,2,2-trichloroethoxycarbonyl or 2-iodoethyoxycarbonyl, optionally substituted 1-phenyl-lower alkoxycarbonyl, for example benzyloxycarbonyl or diphenylmethoxycarbonyl, or aroylmethoxycarbonyl, for example phenacyloxycarbonyl, or the acyl radical of an organic sulphonic acid such as of an aromatic sulphonic acid, above all an optionally substituted phenylsulphonyl radical, in which substituents have, for example, the meaning indicated for the 1-phenyl-lower alkyl radical above, and especially 4-methylphenylsulphonyl, and also an optionally substituted 1-polyphenyl-lower alkyl group, in which substituents, above all in the phenyl part, have, for example, the abovementioned meanings, and above all trityl.

A group $X_5$ which can be replaced by hydrogen is preferably also a group which can be split off by hydrogenolysis, such as one of the abovementioned optionally substituted 1-phenyl-lower alkyl groups and above all benzyl. It can also be one of the acyl groups which can be split off by solvolysis, including alcoholysis, or reduction and has been mentioned for the group $X_4$, and also an optionally substituted aliphatic or araliphatic hydrocarbon radical which is poly-branched at the linking carbon atom, such as tert.-lower alkyl, for example tert.-butyl, or trityl.

A radical which is formed by $X_4$ and $X_5$ together and can be split off is, above all, again a group which can be split off by hydrogenolysis, such as optionally substituted 1-phenyl-lower alkylidene, in which substituents can be, for example, lower alkyl, such as tert.-butyl, hydroxyl, lower alkoxy, halogen and/or nitro, and especially benzylidene, as well as groups which can be split by solvolysis, and especially by hydrolysis, such as lower alkylidene, for example methylene or isopropylidene, or cycloalkylidene, for example cyclohexylidene. A further radical which is formed by the groups $X_4$ and $X_5$ together is the diacyl radical of carbonic acid or thiocarbonic acid, that is to say the carbonyl group or the thiocarbonyl group.

Starting materials which can be used in the form of salts are, above all, used in the form of acid addition salts, especially of corresponding salts with inorganic acids, for example mineral acids, as well as with organic acids.

Radicals $X_4$ and/or $X_5$ which can be split off by hydrogenolysis, especially optionally substituted 1-phenyl-lower alkyl groups and also suitable acyl groups, such as optionally substituted 1-phenyl-lower alkoxycarbonyl, as well as optionally substituted 1-phenyl-lower alkylidene groups formed by the groups $X_4$ and $X_5$ together can be split off by treatment with catalytically activated hydrogen, for example with hydrogen in the presence of a nickel catalyst, such as Raney nickel, or of a suitable noble metal catalyst.

Groups $X_4$ and/or $X_5$ which can be split off by hydrolysis, such as acyl radicals of organic carboxylic acids, for example lower alkanoyl, and half-esters of carbonic acid, for example lower alkoxycarbonyl, and also, for example, trityl radicals, as well as lower alkylidene groups, or a carbonyl group, formed by the radicals $X_4$ and $X_5$ together, can, depending on the nature of such radicals, be split off by treatment with water under acid and/or basic conditions, for example in the presence of a mineral acid, such as hydrochloric acid or sulphuric acid, or of an alkali metal hydroxide or carbonate or alkaline earth metal hydroxide or carbonate.

Radicals which can be split off by acidolysis are, in particular, certain acyl radicals of half-esters of carbonic acid, such as, for example, tert.-lower alkoxycarbonyl or optionally substituted diphenylmethoxycarbonyl radicals and also tert.-lower alkyl radicals $X_5$; they can be split off by treatment with suitable strong organic carboxylic acids, such as lower alkanecarboxylic acids which are optionally substituted by halogen, especially fluorine, and above all with trifluoroacetic acid (if necessary in the presence of an activating agent, such as anisole), and also with formic acid.

Radicals $X_4$ and/or $X_5$ which can be split off by reduction are also understood as those groups which are split off on treatment with a chemical reducing agent (especially with a reducing metal or a reducing metal compound). Such radicals are, in particular, 2-halogeno-lower alkoxycarbonyl or aroylmethoxycarbonyl, which can be split off, for example, on treatment with a reducing heavy metal, such as zinc, or with a reducing heavy metal salt, such as a chromium-II salt, for example chromium-II chloride or chromium-II acetate, usually in the presence of an organic carboxylic acid, such as formic acid or acetic acid, and of water. Arylsulphonyl radicals which can be split off by reduction and especially those which above all represent the radical $X_4$ can be replaced by hydrogen, for example on treatment with an alkali metal, for example lithium or sodium, in ammonia, or by means of electrolytic reduction.

The above reactions are carried out in a manner which is in itself known, usually in the presence of a solvent or solvent mixture, it also being possible for suitable reactants at the same time to act as solvents, and, if necessary with cooling or warming, for example in a temperature range of from about −20° to about +150°, in an open or closed vessel and/or in an atmosphere of an inert gas, for example nitrogen.

The starting materials of the formula VI can be manufactured in a manner which is in itself known, for example by treating a compound of the formula

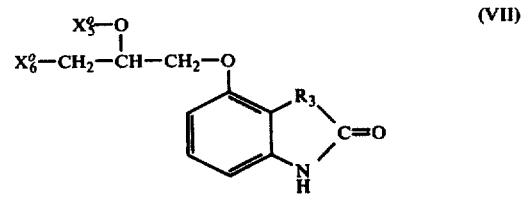

(VII)

with a compound of the formula $R_1$-$X_7^o$ (VIII), in whch $X_5^o$ has the meaning indicated above for $X_5$ and one of the groups $X_6^o$ and $X_7^o$ represents a reactive esterified hydroxyl group and the other represents the group of the formula —NH($X_4$), in which $X_4$ has the abovementioned meaning, with the proviso that at least one of the groups $X_4$ and $X_5$ differs from hydrogen, or in which $X_5^o$ and $X_6^o$ together form a bond and $X_7^o$ represents the group of the formula —$NH(X_4)$, in which $X_4$ differs from hydrogen. The above reactions are carried out in a manner which is in itself known.

The new compounds of the present invention can also be obtained when the radicals $X_8$ and $X_9$ are split off from a compound of the formula

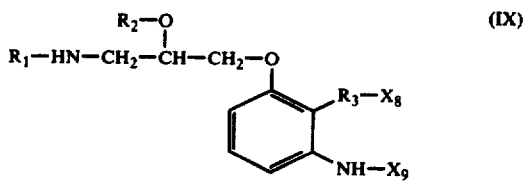

in which $X_8$ and $X_9$ represent radicals which can be split off with the formation of the carbonyl group which, in the compounds of the formula I, is bonded to $R_3$ and the nitrogen atom, or from a salt thereof, with the formation of the carbonyl group and, if desired, the additional process steps are carried out.

The starting material of the formula IX in the form of an acid addition salt is, for example, the acid addition salt with a mineral acid.

Usually, one of the radicals $X_8$ and $X_9$ represents hydrogen, whilst the other denotes the acyl radical of a carbonic acid derivative, such as of a corresponding ester, halide or amide, and represents, for example, lower alkoxycarbonyl, such as methoxycarbonyl or ethoxycarbonyl, or halogenocarbonyl, such as chlorocarbonyl or aminocarbonyl.

The reaction is carried out in the absence or presence of a suitable solvent or diluent, such as an optionally substituted, for example chlorinated, aliphatic, cycloaliphatic or aromatic hydrocarbon, such as benzene, and, if necessary, with cooling or warming, for example in a temperature range of from about 0° to about 100°, in a closed vessel and/or in an inert gas atmosphere, for example a nitrogen atmosphere. Optionally, and if one of the radicals $X_8$ or $X_9$ denotes aminocarbonyl preferably, the reaction is carried out in the presence of a basic condensing agent, say of a metal alcoholate, such as an alkali metal alcoholate, fo example sodium ethylate, in a solvent, say in a lower alkanol, such as ethanol. The reaction is appropriately carried out in a temperature range of about 0°–150° and preferably of 10°–120°.

Starting materials of the formula IX can be manufactured in a manner which is in itself known and optionally in situ. Thus, preferred starting materials can be obtained when, for example, the phenolic hydroxyl group in 2,3-dinitrophenol is converted, such as by treatment with an allyl halide, for example allyl bromide, in the presence of a base, for example potassium carbonate, into the allyloxy group, this is converted, by treating the intermediate product with hydrogen peroxide, for example in the presence of potassium bicarbonate, or with a suitable inorganic or organic percarboxylic acid, for example 3-chloro-perbenzoic acid, into the 2,3-epoxy-propoxy group and the latter is converted, for example by treating the intermediate product with an amine of the formula $R_1$-$NH_2$ (IIIa) into the 3-($R_1$-amino)-2-hydroxy-propoxy group. The two nitro groups in a 3-[3-($R_1$-amino)-2-hydroxy-propoxy]-1,2-dinitrobenzene which is thus obtainable are then reduced to the amino groups, for example by treatment with catalytically activated hydrogen. Reaction with a suitable reactive derivative of carbonic acid, for example a corresponding ester, such as a di-lower alkyl carbonate, for example dimethyl carbonate or diethyl carbonate, a mixed anhydride, such as a carbonic acid dihalide, for example phosgene, or an amide, for example urea or N,N'-carbonyl-diimidazole, gives a preferred starting material, which is preferably formed only in situ and is converted direct into a compound of the formula I.

Within the scope of the definition of the compounds of the formula I, compounds obtained according to the process can be converted in the customary manner into other end products.

Thus, in compounds of the formula I in which $R_2$ represents hydrogen the latter can be replaced by lower alkanoyl in a manner which is in itself known, for example by treating the corresponding compound of the formula I, or preferably a salt, such as a mineral acid addition salt, thereof, with a lower alkanecarboxylic acid or a reactive derivative, such as an anhydride, optionally a mixed anhydride, thereof, for example a halide, such as the chloride, thereof. In this reaction, a ring nitrogen atom can optionally also be acylated; a lower alkanoyl group introduced in this way can be split off selectively, for example by hydrolysis.

Furthermore, in a compound of the formula I in which $R_2$ represents lower alkanoyl, the latter can be split off by solvolysis, for example by means of hydrolysis, and replaced by hydrogen.

Depending on the process conditions and the starting materials, the new compounds are obtained in the free form or in the form of their salts, which is also included in the invention, and the new compounds or salts thereof can also be in the form of hemihydrates, monohydrates, sesquihydrates or polyhydrates. Salts of the new compounds can be converted into the free compounds in the manner which is in itself known, acid addition salts for example, by treatment with basic agents, such as alkali metal hydroxides, carbonates or bicarbonates, or ion exchangers, and metal salts, such as alkali metal salts, which are optionally obtainable according to the process, for example by treatment with acid agents, such as a mineral acid. On the other hand, resulting free compounds can form acid addition salts in a manner which is in itself known, for example by treatment with organic or inorganic acids, such as the abovementioned acids, and the acids used for the manufacture are in particular those acids which are suitable for the formation of salts which can be used pharmaceutically.

These, or other salts, especially acid addition salts of the new compounds, such as, for example picrates or perchlorates, can also be used to purify the resulting free bases, the free compounds being converted into salts, these being separated off and purified and the free compounds being reformed from the salts.

Depending on the choice of the starting materials and procedures, the new compounds can be in the form of optical antipodes or racemates.

Resulting racemates can be resolved into the antipodes according to methods which are in themselves known, for example by recrystallisation from an optically active solvent, by treatment with suitable microorganisms or by reaction with an optically active compound which forms a salt with the racemic compound, especially a corresponding acid, and separation of the salt mixture obtained in this way, for example on the basis of different solubilities, into the diastereomeric salts, from which the free antipodes can be liberated by the action of suitable agents. Optically active acids which are particularly commonly used are, for example, the D and L forms of tartaric acid, di-o-toluyltartaric acid, malic acid, mandelic acid, camphorsulphonic acid, glutamic acid, aspartic acid or quinic acid. Advantageously, the more active of the two antipodes is isolated.

The invention also relates to those embodiments of the process according to which a compound obtainable as an intermediate product at any stage of the process is used as the starting material and the missing process steps are carried out, or the process is discontinued at any stage, or in which a starting material is formed under the reaction conditions, or in which a reactant is optionally present in the form of its salts.

Appropriately, the starting materials used for carrying out the reactions according to the invention are those which lead to the groups of end products mentioned in particular initially and especially to the end products which have been described or singled out specifically.

The new compounds can be used, for example, in the form of pharmaceutical formulations which contain a pharmacologically effective amount of the active substance, optionally together with inorganic or organic, solid or liquid, excipients which can be used pharmaceutically and are suitable for enteral, for example oral, or parenteral administration. Thus, tablets or gelatine capsules are used which contain the active compound together with diluents, for example lactose, dextrose, sucrose, mannitol, sorbitol, cellulose and/or glycine, and/or lubricants, for example silica, talc, stearic acid or salts thereof, such as magnesium stearate or calcium stearate, and/or polyethylene glycol. Tablets can also contain binders, for example magnesium aluminium silicate, starches, such as corn starch, wheat starch, rice starch or arrowroot, gelatine, tragacanth, methylcellulose, sodium carboxymethylcellulose and/or polyvinylpyrrolidone and, if desired, disintegrating agents, for example starches, agar, alginic acid or a salt thereof, such as sodium alginate, and/or effervescent mixtures, or adsorbents, dyestuffs, flavouring substances and sweeteners. Furthermore, the new pharmacologically active compounds can be used in the form of formulations which can be administered parenterally, or of infusion solutions. Such solutions are, preferably, isotonic aqueous solutions or suspensions and these can, for example, be manufactured before use from lyophilised formulations which contain the active compound by itself or together with an excipient, for example mannitol. The pharmaceutical formulations can be sterilised and/or contain auxiliaries, for example preservatives, stabilisers, wetting agents and/or emulsifiers, solubilising agents, salts for regulating the osmotic pressure and/or buffers. The present pharmaceutical formulations which can, if desired, contain further pharmacologically active substances, are manufactured in a manner which is in itself known, for example by means of conventional mixing, granulating, degree-making, dissolving or lyophilising processes, and contain from about 0.1% to 100%, and especially from about 1% to about 50%, of the active compound and lyophilisates contain up to 100% of the active compound.

The dosage can depend on various factors, such as the mode of administration and the species, age and/or state of the individual. In the case of oral administration, the doses to be administered daily are between about 1 mg and about 15 mg for warm-blooded animals weighing about 70 kg.

The examples which follow serve to illustrate the invention; the temperatures are given in degrees Centigrade.

EXAMPLE 1

A mixture of 3.3 g of 4-(2,3-epoxypropoxy)-benzimidazol-2-one in 80 ml of isopropanol and 8.8 g of tert.-butylamine is heated to the boil under reflux for 2 hours. The solvent, together with the excess amine, is then distilled off under reduced pressure. The residual oil which contains 4-(3-tert.-butylamino-2-hydroxy-propoxy)-benzimidazol-2-one is dried at 50°/0.01 mm Hg for 2 hours and dissolved in 30 ml of acetone. 2.5 ml of a 5 N solution of hydrogen chloride in diethyl ether is added to the solution. The crystalline precipitate is recrystallised from a mixture of methanol and acetone. This gives 4-(3-tert.-butylamino-2-hydroxy-propoxy)-benzimidazol-2-one hydrochloride in the form of colourless crystals which melt at 250°–260° with gradual decomposition.

The starting material can be prepared as follows: 225 g of potassium carbonate and 98 g of allyl bromide are added to a solution of 170.0 g of dimethyl 3-hydroxy-phthalate in 400 ml of methyl ethyl ketone. The mixture is heated to the reflux temperature for 18 hours, whilst stirring, and then filtered, the filter residue is washed with methyl ethyl ketone and the filtrate, combined with the wash liquid, is evaporated under reduced pressure. The residual oily crude product is distilled under reduced pressure; dimethyl 3-allyloxyphthalate is obtained as the main fraction; boiling point 126°–130°/0.015 mm Hg.

A mixture of 68.5 g of dimethyl 3-allyloxy-phthalate and 154 ml of a 5 N aqueous solution of sodium hydroxide is heated to the reflux temperature for 3 hours, whilst stirring, and then cooled to a temperature of +10°. 129 ml of 6 N hydrochloric acid are added in portions to the clear reaction solution and during the addition the temperature is not allowed to rise above 20°. After standing for several hours at 0°, the crystalline precipitate is filtered off and washed with a little ice water. After drying at 50°/0.1 mm Hg to constant weight, 3-allyloxy-phthalic acid is obtained; melting point 166°–167°.

A mixture of 45.8 g of 3-allyloxy-phthalic acid in 200 ml of toluene and 25.5 ml of acetic anhydride is heated to the reflux temperature for 3 hours and then evaporated under reduced pressure. The residue is crystallised from diethyl ether and gives 3-allyloxy-phthalic anhydride; melting point 115°–117°.

26 ml of trimethylsilyl azide are added to a suspension of 14.4 g of 3-allyloxy-phthalic anhydride in 100 ml of absolute benzene and the mixture is slowly heated to the boil, whilst stirring, whereupon a vigorous evolution of nitrogen starts. After the reaction has subsided, the mixture is heated to the boil for a further 2 hours, the solvent is then removed under reduced pressure and the residue is dissolved in 50 ml of ethanol and 5 ml of water. The solution is heated to the boil for 18 hours under reflux and then evaporated under reduced pressure. The resulting residue is ground with diethyl ether, whereupon crystallisation takes place. The crystalline product is filtered off, washed with diethyl ether, dried in air and, for further purification, extracted with 100 ml of hot water. The crystals which are insoluble in water are 4-allyloxy-benzimidazol-2-one; melting point 192°–193°.

2.0 g of benzonitrile, 5 ml of 30% strength aqueous hydrogen peroxide and 0.3 g. of potassium bicarbonate are added to a solution of 2.8 g of 4-allyloxy-benzimidazol-2-one in 50 ml of methanol. After stirring for 44 hours at 20°, a crystalline precipitate forms; the reaction mixture is left to stand for one hour at 0° and then filtered. The filter residue is washed with a little cold methanol and then with diethyl ether; 4-(2,3-epoxy-propoxy)-benzimidazol-2-one, which is thus obtainable, melts at 143°–144°.

EXAMPLE 2

After adding 15.2 g of tert.-butylamine, a mixture of 4.6 g of 8-(2,3-epoxy-propoxy)-2,3-dihydro-(4H)-benz[5.6]oxazin-3-one in 150 ml of isopropanol is heated to the boil under reflux for 2 hours. The solvent, together with the excess volatile amine, is then distilled off under reduced pressure. The residue, which contains 8-(3-tert.-butylamino-2-hydroxypropoxy)-2,3-dihydro-(4H)-benz[5.6]oxazin-3-one, is dried at 50°/0.01 mm Hg for 2 hours and then dissolved in methanol and 5 ml of a 5 N solution of hydrogen chloride in diethyl ether are added to the solution. The mixture is evaporated to dryness, acetone is added and 8-(3-tert.-butylamino-2-hydroxypropoxy)-2,3-dihydro-(4H)-benz[5.6]oxazin-3-one hydrochloride is thus obtained as a colourless crystalline product; melting point 182°–183° after recrystallisation from a mixture of methanol and acetone.

The starting material can be prepared as follows:

0.030 g of p-toluenesulphonic acid and 17.8 g of 3,4-dihydro-2H-pyrane are added to a mixture of 29.8 g of 2,3-dihydroxy-nitrobenzene in 400 ml of absolute benzene and the solution is left to stand for 7 days at 20°. It is filtered through 15 g of a silica gel formulation (Merck silica gel 60; grain size 0.063–0.200 mm) and the silica gel is rinsed with benzene. After distilling off the benzene under reduced pressure, a reddish oil is obtained which, when crystallised from hexane, gives 2-hydroxy-3-(tetrahydropyran-2-yloxy)-nitrobenzene in the form of yellow crystals; melting point 72°–73°.

A mixture of 38.4 g of 2-hydroxy-3-(tetrahydropyran-2-yloxy)-nitrobenzene, 22.2 g of potassium carbonate and 27.0 g of ethyl bromoacetate in 400 ml of methyl ethyl ketone is heated to the reflux temperature for 16 hours, whilst stirring, and then filtered; the filter residue is rinsed with 100 ml of methyl ethyl ketone. The combied filtrates are evaporated under reduced pressure. The residual yellowish oil is taken up in 400 ml of diethyl ether, the solution is clarified by filtration, with the addition of 2 g of an active charcoal formulation and the filtrate is evaporated under reduced pressure. The residual oil solidifies after some time to give a mass of crystals and gives 2-ethoxycarbonylmethoxy-3-(tetrahydropyran-2-yloxy)-nitrobenzene; melting point 65°–66°.

108 ml of 2 N hydrochloric acid are added to a solution of 48.5 g of 2-ethoxycarbonylmethoxy-3-(tetrahydropyran-2-yloxy)-nitrobenzene in 972 ml of methanol at 20°. After 1 hour, 216 ml of a 1 N aqueous solution of sodium bicarbonate are added dropwise, whilst stirring. The methanol is distilled off under reduced pressure and 3-nitro-2-ethoxycarbonylmethoxy-phenol crystallises out and is filtered off, washed with water and dried over calcium sulphate under reduced pressure; melting point 49°–50°.

A mixture of 31.7 g of 3-nitro-2-ethoxycarbonylmethoxy-phenol, 18.1 g of potassium carbonate and 17.2 g of allyl bromide in 400 ml of methyl ethyl ketone is heated to the reflux temperature for 16 hours, whilst stirring. The mixture is filtered, the filter residue is rinsed with 100 ml of methyl ethyl ketone and the filtrate, together with the wash liquid, is evaporated under reduced pressure. The yellowish oil consists of 2-ethoxycarbonylmethoxy-3-allyloxy nitrobenzene and is further processed without purification.

A solution of 28.7 g of 2-ethoxycarbonylmethoxy-3-allyoxy-nitrobenzene in 185 ml of glacial acetic acid is warmed to 90°, whilst stirring, and a total of 31 g of iron filings (corroded slightly with hydrochloric acid, and then dried, before use; compare Houben-Weyl, volume 11/1, page 397) and 90 ml of water are then added alternately in portions. The mixture is stirred for a further 1 hour at 90° and filtered, the filter residue is washed with methylene chloride and the filtrate, together with the wash liquid, is evaporated under reduced pressure. The residue is partitioned between ethyl acetate and water; the organic phase is washed with water and a 4 N aqueous solution of sodium carbonate, separated off, dried over sodium sulphate and evaporated under reduced pressure. The crystalline residue is recrystallised from ethanol and gives 8-allyloxy-2,3-dihydro-(4H)-benz[5.6]oxazin-3-one in the form of colourless crystals; melting point 174°–175°.

5.2 g of benzonitrile, 18 ml of a 30 percent strength aqueous solution of hydrogen peroxide and 1.0 g of potassium bicarbonate are added to a suspension of 10.1 g of 8-allyloxy-2,3-dihydro-(4H)-benz[5.6]oxazin-3-one in 400 ml of methanol and the mixture is then stirred for 3 days at 20°. The reaction mixture is then concentrated to a volume of 40 ml under reduced pressure. After leaving to stand at 0°, 8-(2,3-epoxy-propoxy)-2,3-dihydro-(4H)-benz[5.6]oxazin-3-one is obtained in the form of colourless crystals, which are filtered off and washed with a little cold methanol; melting point 158°–160°.

EXAMPLE 3

Tablets containing 0.002 g of 4-(3-tert.-butylamino-2-hydroxy-propoxy)-benzimidazol-2-one hydrochloride are manufactured as follows:

| Composition (for 1,000 tablets): | |
|---|---|
| 4-(3-tert.-Butylamino-2-hydroxy-propoxy)-benzimidazol-2-one hydrochloride | 2.00 g |
| Lactose | 35.00 g |
| Maise starch | 50.00 g |
| Colloidal silica | 6.00 g |
| Talc | 6.00 g |
| Magnesium stearate | 1.00 g |
| Water, q.s. | |

The 4-(3-tert.-butylamino-2-hydroxy-propoxy)-benzimidazol-2-one hydrochloride is mixed with the lactose, part of the maize starch and with colloidal silica and the mixture is forced through a sieve. A further part of the maize starch is mixed to a paste with five times the amount of water on a waterbath and the powder mixture is kneaded with this paste until a slightly plastic mass has formed. This is pressed through a sieve with a mesh width of about 3 mm and dried and the dry granules are again forced through a sieve. The remaining maize starch, the talc and the magnesium stearate are then mixed in and the resulting mixture is pressed to give tablets weighing 0.100 g (with a breaking groove).

In an analogous manner, other compounds of the formula I, or their salts, such as, for example 8-(3-tert.-butylamino-2-hydroxy-propoxy)-2,3-dihydro-(4H)-benz[5.6]oxazin-3-one, 5-(3-tert.-butylamino-2-hydroxy-propoxy)-3,4-dihydro-1H-quinazolin-2-one, 7-(3-tert.-butylamino-2-hydroxy-propoxy)-2(3H)-benzoxazolone, 4-(3-tert.-butylamino-2-hydroxy-propoxy)-3-methyl-benzimidazol-2-one, 4-[3-(1-phenyl-propyl-2-amino)-2-hydroxy-propoxy]-benzimidazol-2-one, 4-[3-(2-(3,4-dimethoxyphenyl)-ethylamino)-2-hydroxy-propoxy]-benzimidazol-2-one and 4-[3-(2-(3,4-methylenedioxyphenyl)-ethylamino)-2-hydroxy-propoxy]-benzimidazol-2-one or their salts, can be used as active compounds in the tablets described.

EXAMPLE 4

After adding 1 g of palladium-on-charcoal catalyst, a solution of 10.9 g of 5-[3-(N-benzyl-tert.-butylamino)-2-hydroxy-propoxy]-3,4-dihydro-1H-quinazolin-2-one in 220 ml of dimethylformamide is hydrogenated under normal conditions until the absorption of hydrogen has ceased. After filtering and evaporating the filtrate, crude crystals of 5-(3-tert.-butylamino-2-hydroxy-propoxy)-3,4-dihydro-1H-quinazolin-2-one with a melting point of 204°-205° are obtained. After passing 1 equivalent of hydrogen chloride into a solution of the compound in a mixture of 150 ml of isopropanol and 50 ml of methanol, the hydrochloride, which has a melting point of 274°-275°, is obtained.

The starting material can be prepared as follows:

(a) A solution of 336 g of 1,3-dinitrobenzene and 174 g of allyl alcohol in 2,000 ml of dioxane is warmed to 40° and a solution of 196 g of potassium cyanide in 400 ml of water is added in the course of about 10 minutes. During the addition the temperature rises to about 60°. The reaction mixture is stirred at 80° for 2 hours, cooled to about 10° and filtered through diatomaceous earth and the filtrate is evaporated. The evaporation residue is dissolved in 2 liters of ethyl acetate and the solution is washed with 5 times 1 liter of water. The dark organic phase is clarified with active charcoal and silica gel. After evaporating off the solvent, a dark red, partially crystalline residue remains and, by crystallisation from isopropanol, this gives 2-allyloxy-6-nitro-benzonitrile with a melting point of 102°-104°. A further amount of the same compound is obtained by chromatography on 2 kg of silica gel and elution with toluene. (Fractions 17-35 with 1 liter of toluene).

(b) 22.5 g of 2-allyloxy-6-nitro-benzonitrile are introduced into a solution of 26.8 g of m-chloroperbenzoic acid (85% strength) in 1 liter of chloroform and the mixture is warmed to 50° in the course of 3 hours. The reaction mixture is kept at this temperature for 24 hours and then cooled and the solution is washed with 100 ml of 1 M sodium sulphite solution, then with 100 ml of 2 N sodium hydroxide solution and finally with 100 ml of water. After drying over magnesium sulphate and evaporating the solution, a colourless crystalline residue is obtained and this is ground with 20 ml of isopropanol, the mixture is filtered and the material on the filter is dried in vacuo, after which crude 2-(2,3-epoxypropoxy)-6-nitro-benzonitrile with a melting point of 131°-135° is obtained and this is used further in the form of the crude product.

(c) A suspension of 23.4 g of 2-(2,3-epoxy-propoxy)-6-nitro-benzonitrile and 34.6 g of N-benzyl-tert.-butylamine in 550 ml of isopropanol is warmed under reflux until a solution forms and this is then heated under reflux for a further 8-10 hours. On cooling, 1-(N-benzyl-tert.-butylamino)-3-(2-cyano-3-nitro-phenoxy)-2-propanol with a melting point of 120°-122° crystallises out; a further amount of this compound is obtained by concentrating the filtrate.

(d) 28.0 g of 1-(N-benzyl-tert.-butylamino)-3-(2-cyano-3-nitro-phenoxy)-2-propanol are dissolved in 350 ml of ethanol in a flask provided with a stirrer, a reflux condenser and a dropping funnel, by heating to the boil. After adding about 0.5 ml of a suspension of Raney nickel, a solution of 18.2 g of hydrazine hydrate in 20 ml of ethanol is added dropwise, whilst the mixture is boiling, at such a rate that vigorous evolution of gas starts. After the addition is complete, the mixture is heated to the boil for a further half hour. The reaction mixture is then cooled and filtered through diatomaceous earth and the filtrate is evaporated. The residual oil is crude 6-[2-hydroxy-3-(N-benzyl-tert.-butylamino)-propoxy]-anthranilamide and is further processed without further purification.

(e) A solution of 27 g of 6-[2-hydroxy-3-(N-benzyl-tert.-butylamino)-propoxy]-anthranilamide in 400 ml of tetrahydrofurane is added dropwise, under nitrogen, to a suspension of 8.3 g of lithium aluminium hydride in 100 ml of tetrahydrofurane. After stirring for 20 hours under reflux, a further 8.0 g of lithium aluminium hydride are added and the mixture is again heated to the boil for 60-65 hours. Whilst cooling with ice, the excess lithium aluminium hydride is decomposed by means of 17 ml of concentrated sodium hydroxide solution and 40 ml of water. The precipitate is filtered off and washed with 50 ml of tetrahydrofurane and the combined filtrates are evaporated. This gives crude 2-aminomethyl-3-[2-hydroxy-3-(N-benzyl-tert.-butylamino)-propoxy]-aniline in the form of an oil which, on dissolving in methanol and passing hydrogen chloride into the solution until it gives an acid reaction, gives the hydrochloride which has a melting point of 260°-265°.

(f) 5.3 g of methyl chloroformate are added dropwise to a solution of 16.2 g of 2-aminomethyl-3-[2-hydroxy-3-(N-benzyl-tert.-butylamino)-propoxy]-aniline in a mixture of 150 ml of isopropanol and 150 ml of water, at 15°-20°, whilst stirring and cooling with ice. The reaction mixture is stirred at room temperature for a further 2 hours and then evaporated. The residue is dissolved in 100 ml of water, the solution is extracted with 50 ml of ether and the aqueous phase is rendered alkaline with concentrated ammonia and extracted 3 times with, in each case, 200 ml of ethyl acetate. The residue which remains after evaporating the organic phase is dissolved in 50 ml of methanol and boiled with 4.86 g of sodium methylate under reflux for 3 hours. The crystalline precipitate which gradually forms is filtered off after cooling the reaction mixture in an ice bath, whereupon 5-[3-(N-benzyl-tert.-butylamino)-2-hydroxy-propoxy]-3,4-dihydro-1H-quinazolin-2-one with a melting point of 215°-217° is obtained.

EXAMPLE 5

Analogously to Example 4 f), 8.0 g of 2-aminomethyl-3-(3-tert.-butylamino-2-hydroxy-propoxy)-aniline are reacted first with 3.3 g of methyl chloroformate in a mixture of 28 ml of isopropanol and 28 ml of water and then with 3.2 g of sodium methylate in 30 ml of methanol. After working up, 5-(3-tert.-butylamino-2-hydroxy-propoxy)-3,4-dihydro-1H-quinazolin-2-one with a melting point of 204°-205° is obtained.

The starting material can be prepared in the following way:

(a) A mixture of 11.0 g of the 2-(2,3-epoxypropoxy)-6-nitro-benzonitrile obtained according to Example 4(b) and 18.5 g of tert.-butylamine in 300 ml of isopropanol is heated under reflux for 5–6 hours. After evaporating, a crystalline residue remains and this is stirred with 20 ml of carbon tetrachloride and the mixture is then filtered, whereupon 1-tert.-butylamino-3-(2-cyano-3-nitro-phenoxy)-2-propanol with a melting point of 115°–118° is obtained.

(b) 12.2 g of 1-tert.-butylamino-3-(2-cyano-3-nitro-phenoxy)-2-propanol are reacted in 200 ml of ethanol with 11 g of hydrazine hydrate and Raney nickel, analogously to Example 4(d), and after filtering and evaporating the filtrate, this gives crude 6-(3-tert.-butylamino-2-hydroxy-propoxy)-anthranilamide in the form of an oil which is used further without further purification.

(c) 12 g of crude 6-(3-tert.-butylamino-2-hydroxy-propoxy)-anthranilamide are dissolved in 400 ml of tetrahydrofurane and reduced, analogously to Example 4(e), with 6.1 g of lithium aluminium hydride for 48 hours. After working up, 2-aminomethyl-3-(3-tert.-butylamino-2-hydroxy-propoxy)-aniline is obtained in the form of an oil which is further used as such. It forms a tri-hydrochloride with a melting point of 250°–260° (with sublimation).

EXAMPLE 6

After adding 1 g of palladium-on-charcoal catalyst (5% strength), a solution of 7.0 g of 5-[3-(N-benzyl-tert.-butylamino)-2-hydroxy-propoxy]-(1H)(3H)-quinazoline-2,4-dione in 200 ml of 2-methoxy-ethanol is hydrogenated under normal conditions until the calculated amount of hydrogen has been taken up. After filtering and evaporating the solvent, a crystalline residue remains and this is stirred with 10 ml of isopropanol and the mixture is then filtered, whereupon 5-(3-tert.-butylamino-2-hydroxy-propoxy)-(1H)(3H)-quinazoline-2,4-dione with a melting point of 271°–275° is obtained. The hydrochloride melts at 298°–305° (with decomposition).

The starting material can be prepared in the following way:

(a) 16 g of the crude 6-[3-(N-benzyl-tert.-butylamino)-2-hydroxy-propoxy]-anthranilamide obtained according to Example 4(d) are dissolved in 45 ml of glacial acetic acid and a solution of 7.45 g of potassium cyanate in 23 ml of water is added. Due to the exothermic reaction which starts, the internal temperature of the reaction mixture rises to 41°. The solution is stirred for a further 4 hours at room temperature and poured into 200 L ml of water and the mixture is rendered alkaline with 2 N sodium carbonate solution. The crystals of 2-[3-(N-benzyl-tert.-butylamino)-2-hydroxy-propoxy]-6-ureido-benzamide which have precipitated out are filtered off and recrystallised from a little isopropanol; melting point (158°), 163°–167°.

(b) 9.7 g of 2-[3-(N-benzyl-tert.-butylamino)-2-hydroxy-propoxy]-6-ureido-benzamide are added to a solution of 0.65 g of sodium in 100 ml of absolute ethanol and the suspension is heated under reflux and whilst stirring until no further elimination of ammonia can be observed (about 5–6 hours). The suspension is cooled and the crystals are filtered off and washed with 20 ml of ethanol and then with 20 ml of water. After drying in vacuo at 90° for 14 hours, the 5-[3-(N-benzyl-tert.-butylamino)-2-hydroxy-propoxy]-(1H)(3H)-quinazoline-2,4-dione which is thus obtained melts at 190°–192°.

EXAMPLE 7

3.24 g of 2-(3-tert.-butylamino-2-hydroxy-propoxy)-6-ureido-benzamide are boiled with a solution of 0.28 g of sodium in 150 ml of absolute ethanol for 1.5 hours under reflux, the reaction mixture is evaporated and the residue is dissolved in 50 ml of water. After neutralising the aqueous solution with 2 N hydrochloric acid, the mixture is filtered, the filtrate is evaporated and the residue is extracted by boiling with 100 ml of methanol. The undissolved material is filtered off and the filtrate is evaporated, whereupon 5-(3-tert.-butylamino-2-hydroxy-propoxy)-(1H)(3H)-quinazoline-2,4-dione is obtained in the form of the hydrochloride with a melting point of 298°–305° (with decomposition).

The starting material can be prepared in the following way:

(a) 6.2 g of the 2-[3-(N-benzyl-tert.-butylamino)-2-hydroxy-propoxy]-6-ureido-benzamide obtained according to Example 6(a) are hydrogenated in 500 ml of methanol in the presence of 0.6 g of palladium-on-charcoal catalyst (5% strength) until the absorption of hydrogen has ceased. 2-(3-tert.-Butylamino-2-hydroxy-propoxy]-6-ureido-benzamide with a melting point of 189°–191° is obtained by filtering the mixture, evaporating the filtrate and adding isopropanol to the residue.

EXAMPLE 8

3.7 g of 7-[3-(N-benzyl-tert.-butylamino)-2-hydroxy-propoxy]-2-(3H)-benzoxazolone are hydrogenated under normal conditions in 70 ml of methanol with the addition of 0.4 g of palladium-on-charcoal catalyst until the absorption of hydrogen has ceased. After filtering off the catalyst, the filtrate is neutralised with a 5 N solution of hydrogen chloride in ethanol and evaporated and the residual oil is made to crystallise with acetone. This gives 7-(3-tert.-butylamino-2-hydroxy-propoxy)-2(3H)-benzoxazolone hydrochloride, which after recrystallisation from methanol/acetone melts at 221°–224°.

The starting material can be prepared as follows:

(a) 125 g of finely powdered, dried silver nitrate are added in portions to a solution of 140 g of o-allyloxyphenyl acetate and 100 ml of acetyl chloride in 300 ml of freshly distilled carbon tetrachloride, at −5° to −15°, whilst stirring and cooling with an ice/sodium chloride bath. The temperature of the reaction mixture is allowed to rise gradually to 20° in the course of 3 hours, the mixture is filtered and the filtrate is washed with a saturated solution of urea in water and evaporated. This gives a light brown oily residue which is chromatographed in 250 ml fractions over 800 g of silica gel using toluene. Fractions 1–4 are discarded. The component which boils at 125°–135°/0.1 mm Hg and is phenyl 2-allyloxy-3-nitro-acetate is isolated from fractions 5 and 6 and 7–11.

(b) 31.0 g of the compound obtained according to (a) are dissolved in 200 ml of ethanol, 40 ml of a 10 N solution of hydrogen chloride in ethanol are added and the mixture is heated to the boil under reflux for 2 hours. After evaporating the solution, washing the residue with water and distilling under 0.06 mm Hg, 2-allyloxy-3-nitrophenol which boils at 90°–103°/0.06 mm Hg is obtained.

(c) 10.0 g of 2-allyloxy-3-nitrophenol, 27 g of potassium carbonate and 54 ml of epichlorohydrin in 300 ml of acetone are stirred under reflux for 15–20 hours. After filtering the reaction mixture and evaporating the filtrate, crude 2-allyloxy-1-(2,3-epoxy-propoxy)-3-nitrobenzene is obtained and this can be used further as such.

(d) 14 g of crude 2-allyloxy-1-(2,3-epoxy-propoxy)-3-nitrobenzene and 11.0 g of N-benzyl-tert.-butylamine in 70 ml of isopropanol are boiled under reflux for 7 hours. After neutralising with concentrated hydrochloric acid, 1-[2-allyloxy-3-nitro-phenoxy)-3-(N-benzyl-tert.-butylamino)-2-propanol crystallises out in the form of the hydrochloride and after recrystallisation from methanol/isopropanol this melts at 206°–209° with the evolution of gas. The base is an oil.

(e) A solution of 19.4 g of 1-(2-allyloxy-3-nitrophenoxy)-3-(N-benzyl-tert.-butylamino)-2-propanol in a mixture of 350 ml of ethanol, 35 ml of water and 5 ml of triethylamine, with the addition of 1 g of rhodium tris-(triphenylphosphine)-chloride, is stirred under reflux for 45 minutes. After filtering and evaporating the filtrate, crude 1-(N-benzyl-tert.-butylamino)-3-(2-hydroxy-3-nitro-phenoxy)-2-propanol is obtained in the form of a dark red oil, which is used further without further purification.

(f) A solution of 16.1 g of crude 1-(N-benzyl-tert.-butylamino)-3-(2-hydroxy-3-nitro-phenoxy)-2-propanol in 150 ml of ethanol is reduced, analogously to Example 4(d), with 15 ml of hydrazine hydrate and Raney nickel to give 1-(N-benzyl-tert.-butylamino)-3-(3-amino-2-hydroxy-phenoxy)-2-propanol. The base forms a dark oil which is used further without further purification. The base crystallises from ether as greenish crystals with a melting point of 105°–110°.

(g) 14.5 g of 1-(N-benzyl-tert.-butylamino)-3-(3-amino-2-hydroxy-phenoxy)-2-propanol are dissolved in 140 ml of an isopropanol/water mixture (1:1) and 5.0 ml of methyl chloroformate are added, at 15°–20°, whilst stirring vigorously and stirring is continued for a further 1½ hours at room temperature, the reaction mixture is then evaporated and the residue is dissolved in 50 ml of water. After extraction with 20 ml of ethyl acetate, the acid aqueous phase is rendered alkaline with concentrated sodium hydroxide solution and extracted with 3 times 100 ml of methylene chloride. Evaporation of the organic phase gives the crude base, from which crystalline 1-(N-benzyl-tert.-butylamino)-3-(2-hydroxy-3-methoxycarbonylamino-phenoxy)-2-propanol with a melting point of 130°–133° is isolated.

(h) 6.4 g of 1-(N-benzyl-tert.-butylamino)-3-(2-hydroxy-3-methoxycarbonylamino-phenoxy)-2-propanol are introduced in portions, at 10°–°, into an ice-cooled suspension of 1.0 g of a 50% strength dispersion of sodium hydride in 1,2-dimethoxyethane and the mixture is heated under reflux for 1 hour. The reaction mixture is evaporated and the residue is partitioned between 1.5 ml of glacial acetic acid, 10 ml of water and 100 ml of ethyl acetate. The aqueous phase is again extracted with 100 ml of ethyl acetate. After evaporation, the combined ethyl acetate extracts give a crude base which is purified via the neutral fumarate which has a melting point of 202°–206°.

EXAMPLE 9

A mixture of 2.6 g of 7-(2,3-epoxy-propoxy)-4H-1,3-benzoxazin-2(1H)-one, 75 ml of isopropanol and 7.6 g of tert.-butylamine is reacted analogously to Example 2. After working up, the residue is recrystallised from a mixture of methanol and acetone, whereupon 7-(3-tert.-butylamino-2-hydroxypropoxy)-4H-1,3-benzoxazin-2(1H)-one hydrochloride with a melting point of 243°–244° is obtained.

The starting material can be prepared as follows:

(a) 3.14 ml of boron tribromide are added to a solution of 24.6 g of 2-nitro-6-methoxybenzyl bromide in 50 ml of methylene chloride at 0° and the reaction mixture is then left to stand for one hour at 20° and is then stirred for 20 hours under reflux. The reaction mixture is then evaporated under reduced pressure, the residue is dissolved in 100 ml of glacial acetic acid, 40 g of anhydrous sodium acetate are added and the mixture is heated to the boil for 10 minutes, whilst stirring. The mixture is then poured into 500 ml of ice water and extracted three times with ether. The ether extract is washed with aqueous sodium bicarbonate solution, dried over sodium sulphate and evaporated. On grinding with hexane, the oily residue gives 2-nitro-6-hydroxybenzyl acetate; melting point 113°–114°.

(b) A mixture of 24.9 g of 2-nitro-6-hydroxybenzyl acetate, 150 ml of methyl ethyl ketone, 11.4 ml of allyl bromide and 18.1 g of potassium carbonate is stirred under reflux for 5 hours. After cooling, the inorganic salts are filtered off, the residue is rinsed with methyl ethyl ketone and the filtrate is evaporated under reduced pressure. The residual oil is dissolved in benzene and the solution is chromatographed over 300 g of silica gel 60 (Merck, grain size 0.063–0.20 mm). The fractions containing the product are combined and evaporated, whereupon 2-nitro-6-allyloxy-benzyl acetate is obtained as an oil.

(c) 11 ml of 2 N sodium hydroxide solution are added to a solution of 5.2 g of 2-nitro-6-allyloxy-benzyl acetate in 90 ml of methanol and the mixture is heated to 60° for half an hour. The methanol and part of the water are then distilled off under reduced pressure, the residue is partitioned between water and diethyl ether and the ethereal phase is washed with water, dried over sodium sulphate and evaporated under reduced pressure, whereupon 2-nitro-6-allyloxy-benzyl alcohol is obtained as a yellowish oil.

(d) A mixture of 1 g of Raney nickel and 100 ml of methanol is initially introduced into a reaction vessel and warmed to an internal temperature of 50°–60°. A solution of 4.4 g of 2-nitro-6-allyloxy-benzyl alcohol and 5 ml of hydrazine hydrate in 40 ml of methanol are allowed to run in dropwise in the course of 15 minutes, whilst stirring. After the evolution of gas, which initially is vigorous, has subsided, the mixture is heated under reflux for a further 15 minutes, the catalyst is filtered off and the filtrate is evaporated, whereupon 2-amino-6-allyloxy-benzyl alcohol is obtained as a brownish oil.

(e) A solution of 3.1 g of 2-amino-6-allyloxy-benzyl alcohol in 80 ml of methylene chloride is initially introduced, together with a solution of 2.2 g of sodium bicarbonate in 100 ml of water, into a reaction vessel. The mixture is cooled to an internal temperature of 0° and a solution of 2.8 ml of benzyloxy-carbonyl chloride in 20 ml of methylene chloride is allowed to run in dropwise in the course of 20 minutes, whilst stirring, at such a rate that the temperature does not rise above 0°. The reaction mixture is then stirred for 1½ hours at 0° and the organic phase is then separated off, dried over sodium sulphate and evaporated under reduced pressure, whereupon crude 2-benzyloxycarbonylamino-6-allyloxybenzyl alcohol is obtained as a brownish oil.

(f) 1.7 ml of a 1 N solution of sodium ethoxide in ethanol are added to a solution of 5.9 g of 2-benzyloxycarbonylamino-6-allyloxy-benzyl alcohol in 10 ml of absolute ethanol and the mixture is then heated to the boil under reflux for 30 minutes. The solvent is then distilled off under reduced pressure, 1.7 ml of 1 N hydrochloric acid are added to the residue and the mixture is partitioned between methylene chloride and water. The organic phase is separated off, washed with water, dried over sodium sulphate and filtered and the filtrate is evaporated. The crystalline residue is recrystallised from diethyl ether, whereupon 7-allyloxy-4H-1,3-benzoxazin-2(1H)-one with a melting point of 157°-158° is obtained.

(g) 2.0 g of benzonitrile, 5 ml of 30% strength aqueous hydrogen peroxide and 0.3 g of potassium bicarbonate are added to a solution of 1.5 g of 7-allyloxy-4H-1,3-benzoxazin-2(1H)-one in 60 ml of methanol. After stirring at 20° for 60 hours, the solvent is largely distilled off under reduced pressure. The crystals which have precipitated out are filtered off and recrystallised from methanol, whereupon 7-(2,3-epoxypropoxy)-4H-1,3-benzoxazin-2(1H)-one with a melting point of 141°-143° is obtained.

EXAMPLE 10

4-(3-tert.-Butylamino-2-hydroxy-propoxy)-3-butyl-benzimidazol-2-one, the hydrochloride of which, after recrystallisation from a mixture of methanol and acetone, melts at 226°-227°, is obtained analogously to Example 1 from 4.0 g of 4-(2,3-epoxypropoxy)-3-butyl-benzimidazol-2-one and 16 ml of tert.-butylamine in 160 ml of isopropanol.

4-(2,3-Epoxy-propoxy)-3-butylbenzimidazol-2-one which is used as the starting material, can be prepared as follows:

(a) A mixture of 9.0 g of 1-allyloxy-2,3-dinitrobenzene and 40 ml of n-butylamine in 400 ml of isopropanol is heated under reflux, and stirred, for two hours. After evaporating off the solvent and the excess n-butylamine under reduced pressure, the resulting oil is dried at 50°/0.01 mm Hg for 2 hours. The 1-allyloxy-2-butylamino-3-nitrobenzene which is thus obtained can be further used without purification.

(b) A suspension of 0.5 g of Raney nickel in 50 ml of tetrahydrofurane is warmed to 50°, whilst stirring, and a solution of 10.0 g of 1-allyloxy-2-butylamino-3-nitrobenzene and 10 ml of hydrazine hydrate in 100 ml of tetrahydrofurane is added dropwise in the course of 40 minutes. The reaction mixture is then heated to the boil for 1 hour, whilst stirring and under reflux. After cooling, the catalyst is filtered off, the filtrate is evaporated under reduced pressure and the oily residue is subjected to distillation in a bulb tube, 1-allyloxy-2-butylamino-3-aminobenzene being obtained at 100°/0.1 mm Hg (external temperature) as a yellowish distillate.

(c) A mixture of 7.7 g of 1-allyloxy-2-butylamino-3-aminobenzene and 7.1 g of N,N'-carbonyldiimidazole in 100 ml of toluene is stirred at 60° for 15 hours. The toluene is then distilled off under reduced pressure and the residue is extracted several times with water and then partitioned between water and diethyl ether. The organic phase is dried over sodium sulphate and partially evaporated, whereupon crystalline 4-allyloxy-3-butyl-benzimidazol-2-one with a melting point of 110°-112° is obtained.

(d) 2.2 g of benzonitrile, 5.4 ml of a 30 percent strength aqueous solution of hydrogen peroxide and 0.3 g of potassium bicarbonate are added to a suspension of 3.3 g of 4-allyloxy-3-butyl-benzimidazol-2-one in 90 ml of methanol and the mixture is then stirred for 3 days at 20°. The methanol is then virtually completely distilled off under reduced pressure, the residual oil is partitioned between water and diethyl ether and the organic phase is washed with water, dried over sodium sulphate and concentrated to a volume of about 15 ml and petroleum ether is added. The resulting crystals are recrystallised from a diethyl ether/hexane mixture, whereupon 4-(2,3-epoxypropoxy)-3-butyl-benzimidazol-2-one with a melting point of 90°-92° is obtained.

EXAMPLE 11

4-(3-Isopropylamino-2-hydroxypropoxy)-benzimidazol-2-one, the hydrochloride of which is recrystallised from a mixture of methanol and acetone and has a melting point of 231°-232°, is obtained analogously to Example 1 from 6.6 g of 4-(2,3-epoxypropoxy)-benzimidazol-2-one and 20.2 ml of isopropylamine in 160 ml of isopropanol.

EXAMPLE 12

4-(3-tert.-Butylamino-2-hydroxypropoxy)-3-methyl-benzimidazol-2-one, the hydrochloride of which, after recrystallisation from a mixture of methanol and acetone, melts at 246°-248° (with decomposition), is obtained analogously to Example 1 from 2.85 g of 4-(2,3-epoxypropoxy)-3-methyl-benzimidazol-2-one and 15 ml of tert.-butylamine in 150 ml of isopropanol.

4-(2,3-Epoxypropoxy)-3-methyl-benzimidazol-2-one which is used as the starting material, can be prepared as follows:

(a) A mixture of 9.0 g of 1-allyloxy-2,3-dinitrobenzene, 400 ml of isopropanol and 12.4 g of gaseous methylamine is heated, in a pressure vessel, to 90° for 3 hours, whilst stirring. After cooling and letting-down, the reaction solution is evaporated under reduced pressure. The resulting oil is dried at 50°/0.01 mm Hg for 2 hours, whereupon 1-allyloxy-2-methylamino-3-nitrobenzene is obtained; this can be used further without purification.

(b) 1-Allyloxy-2-methylamino-3-aminobenzene, which after distillation in a bulb tube is obtained at 110°-120°/0.1 mm Hg (external temperature) as a yellowish oil, is obtained analogously to Example 10b) from 7.1 g of 1-allyloxy-2-methylamino-3-nitrobenzene by reduction by means of 10 ml of hydrazine hydrate and 0.5 g of Raney nickel using the same amount of tetrahydrofurane as the solvent.

(c) 4-Allyloxy-3-methyl-benzimidazol-2-one, which has a melting point of 167°-168°, is obtained analogously to Example 10c) from 5.4 g of 1-allyloxy-2-methylamino-3-aminobenzene and 6.1 g N,N'-carbonyldiimidazole in 100 ml of toluene, after working up and subsequently recrystallising from toluene.

(d) Analogously to Example 10d), 2.55 g of 4-allyloxy-3-methyl-benzimidazol-2-one are reacted in a mixture of 90 ml of methanol, 2.0 g of benzonitrile, 5.0 ml of a 30 percent strength aqueous solution of hydrogen peroxide and 0.3 g of potassium bicarbonate. After removing the methanol, a crystalline precipitate is obtained on the addition of water and after recrystallisation from aqueous methanol this gives 4-(2,3-epoxypropoxy)-3-methyl-benzimidazol-2-one which has a melting point of 165°-166°.

EXAMPLE 13

A mixture of 4.12 g of 4-(2,3-epoxypropoxy)benzimidazol-2-one in 100 ml of isopropanol and 13.52 g of d,1-1-phenyl-2-aminopropane is heated to the boil under reflux for 4 hours. The solvent is then distilled off under reduced pressure and subsequently the excess 1-phenyl-2-aminopropane is distilled off at 50°/0.01 mm Hg. The residue is dissolved in isopropanol and a solution of the equimolar amount of fumaric acid in isopropanol is added, whereupon the 1:1 4-[3-(1-phenylpropyl-2-amino)-2-hydroxy-propoxy]-benzimidazol-2-one fumarate crystallises out; melting point 186°-188°.

EXAMPLE 14

A mixture of 4.12 g of 4-(2,3-epoxypropoxy)-benzimidazol-2-one in 50 ml of isopropanol and 4.0 g of dibenzylamine is heated under reflux for 5 hours. The solvent is then distilled off under reduced pressure and the residue is recrystallised from ethyl acetate, whereupon 4-(3-dibenzylamino-2-hydroxypropoxy)-benzimidazol-2-one with a melting point of 201°-202° is obtained.

EXAMPLE 15

0.6 ml of glacial acetic acid and 3.7 ml of acetone are added to a solution of 4.0 g of 4-(3-dibenzylamino-2-hydroxypropoxy)-benzimidazol-2-one in 300 ml of ethanol. This solution is added to a pre-hydrogenated suspension of 0.5 g of 10 percent strength palladium oxide-on-charcoal and 0.5 g of 10 percent strength platinum oxide-on-charcoal. The suspension is shaken under hydrogen. After the absorption of hydrogen has ceased, the catalyst is filtered off and rinsed with ethanol and the filtrate is evaporated under reduced pressure. The oily residue is partitioned between 10 ml of a saturated aqueous solution of sodium carbonate and 50 ml of ethyl acetate. The organic phase is washed with a half-saturated aqueous solution of sodium chloride, dried over sodium sulphate and then evaporated under reduced pressure. The residue is dissolved in acetone and an ethereal solution of hydrogen chloride is added. 4-(3-Isopropylamino-2-hydroxypropoxy)-benzimidazol-2-one hydrochloride is obtained and after recrystallisation from methanol/acetone this melts at 231°-233° with decomposition.

EXAMPLE 16

1.7 ml of concentrated hydrochloric acid and then 10 ml of a molar solution of phosgene in toluene are added to 2.5 g of 1-(2,3-diaminophenoxy)-2-hydroxy-3-tert.-butylaminopropane and the mixture is stirred for 5 hours at 20°. After adding a further 10 ml of the phosgene solution, the mixture is stirred for a further 18 hours. The solvent is then distilled off under reduced pressure. The residue is recrystallised from a mixture of methanol and acetone, whereupon 4-(3-tert.-butylamino-2-hydroxypropoxy)-benzimidazol-2-one hydrochloride with a melting point of 250°-260° (gradual decomposition) is obtained.

1-(2,3-Diamino-phenoxy)-2-hydroxy-3-tert.-butylaminopropane, which is used as the starting material, can be prepared as follows:

(a) A mixture of 65.1 g of 2,3-dinitrophenol, 300 ml of acetone and 47.1 g of potassium carbonate is heated under reflux, whilst stirring, and 29 ml of allyl bromide are allowed to run in dropwise in the course of one hour. After stirring and heating under reflux for a further 16 hours, the inorganic salts are filtered off and the residue is rinsed with acetone. The filtrate is evaporated under reduced pressure, the residue is taken up in diethyl ether and petroleum ether is added to the solution, whereupon 1-allyloxy-2,3-dinitrobenzene with a melting point of 51°-52° crystallises out.

(b) 4.6 g of potassium bicarbonate, 36.0 g of benzonitrile and 60 ml of 30% strength hydrogen peroxide are added to a solution of 52.2 g of 1-allyloxy-2,3-dinitrobenzene in 450 ml of methanol and the mixture is then stirred for 4 days at 22°. The resulting crystalline precipitate is filtered off and recrystallised from methanol, whereupon 1-(2,3-dinitrophenoxy)-2,3-epoxypropane with a melting point of 98°-100° is obtained.

(c) Dry carbon dioxide is passed into a solution of 11.4 ml of tert.-butylamine in 40 ml of diethyl ether and a white crystalline precipitate forms. Carbon dioxide continues to be passed in until the bulk of the ether has volatilised. 24.0 g of 1-(2,3-dinitrophenoxy)-2,3-epoxypropane and 300 ml of isopropanol are added to the resulting residue and the mixture is heated to the reflux temperature for one hour, whilst stirring, a clear solution being obtained. The latter is evaporated under reduced pressure and the crystalline residue is recrystallised from toluene, whereupon 1-(2,3-dinitrophenoxy)-2-hydroxy-3-tert.-butylaminopropane with a melting point of 124°-125° is obtained.

(d) A suspension of 0.5 g of Raney nickel in 20 ml of ethanol is warmed to an internal temperature of 65°-70°, whilst stirring. A solution of 2.3 g of 1-(2,3-dinitrophenoxy)-2-hydroxy-3-tert.-butylaminopropane in 40 ml of tetrahydrofurane and a solution of 3.6 ml of hydrazine hydrate in 40 ml of ethanol are allowed simultaneously to run dropwise, from two dropping funnels, into this suspension. The mixture is then stirred for a further 2 hours at 65°-70°, the catalyst is then filtered off, the filtrate is evaporated under reduced pressure, the residue is dissolved in diethyl ether and the ether solution is treated with active charcoal and filtered. After concentrating the filtrate, 1-(2,3-diaminophenoxy)-2-hydroxy-3-tert.-butylaminopropane with a melting point of 73°-75° is obtained on the addition of petroleum ether.

EXAMPLE 17

Analogously to Example 13, 4-[3-(2-(3,4-dimethoxyphenyl)-ethylamino)-2-hydroxypropoxy]-benzimidazol-2-one is obtained from 2.8 g of 4-(2,3-epoxypropoxy)-benzimidazol-2-one and 12.3 g of 2-(3,4-dimethoxyphenyl)-ethylamine and is dissolved in acetone and an ethereal solution of hydrogen chloride is added to this solution, whereupon the hydrochloride is obtained and this is recrystallized from methanol/acetone; melting point 230°-232°.

EXAMPLE 18

After adding 2.0 g of palladium-on-charcoal catalyst (5% strength), a solution of 3.22 g of 5-(3-benzylisopropylamino-2-hydroxypropoxy)-1,2,3,4-tetrahydro-2,3-dioxo-quinoxazoline hydrochloride hemi-hydrate in 60 ml of water is hydrogenated at room temperature and under a pressure of 4 atmospheres. After about 15 hours, the calculated amount of hydrogen has been taken up. The reaction mixture is separated from the catalyst by filtration and the filtrate is evaporated completely under a waterpump vacuum, whereupon 5-(3-isopropylamino-2-hydroxypropoxy)-1,2,3,4-tetrahydro-2,3-dioxoquinoxazoline hydrochloride with a melting point of 290°-294° (decomposition) is obtained.

Recrystallisation from methanol/ether gives the compound with a melting point of 293°-295° (decomposition).

The starting material used can be prepared as follows:

(a) A solution of 5.3 g of 4-(2,3-epoxypropoxy)-benz-2,1,3-thiadiazole and 3.8 g of N-benzylisopropylamine in 100 ml of isopropanol is boiled under reflux for 4 hours. The reaction mixture is evaporated under a waterpump vacuum, the residue is dissolved in ether and the solution is extracted with 2 N hydrochloric acid. The combined hydrochloric acid extracts are rendered alkaline with concentrated ammonia and extracted with ether. The combined ether extracts are washed with water, dried over sodium sulphate and evaporated under a waterpump vacuum, whereupon 4-(3-benzylisopropylamino-2-hydroxypropoxy)-benz-2,1,3-thiadiazole is obtained as a yellow oil.

(b) 12.8 g of zinc dust are introduced in 3 portions into a solution of 8.7 g of 4-(3-benzylisopropylamino-2-hydroxypropoxy)-benz-2,1,3-thiadiazole in 110 ml of glacial acetic acid, at room temperature, whilst stirring. After stirring for about 3 hours at room temperature, the reaction mixture is separated from the excess zinc dust by filtration and the filtrate is evaporated completely under a waterpump vacuum. 15% strength sodium hydroxide solution is added to the residue and the mixture is extracted with methylene chloride. The combined methylene chloride extracts are washed with water, dried over sodium sulphate and evaporated under a waterpump vacuum, whereupon 3-(3-benzylisopropylamino-2-hydroxypropoxy)-1,2-phenylenediamine with a melting point of 60°-63° is obtained.

(c) 8 g of 3-(3-benzylisopropylamino-2-hydroxypropoxy)-1,2-phenylenediamine are stirred with 40 ml of dimethyl oxalate at 100° for 15 hours. The crystals which have precipitated are filtered off and washed with ether. The resulting crystals are dissolved in 50 ml of methanol and the solution is stirred with 5 ml of 2 N sodium hydroxide solution at 60° for 2 hours. The resulting suspension is acidified with 2 N hydrochloric acid and the methanol is evaporated in vacuo. The clear solution containing hydrochloric acid is neutralised with sodium bicarbonate solution, after which the crystals which have precipitated and are 5-(3-benzylisopropylamino-2-hydroxypropoxy)-1,2,3,4-tetrahydro-2,3-dioxo-quinoxazoline with a melting point of 263°-267° (decomposition) are separated off. The hydrochloride prepared with methanolic hydrochloric acid crystallises from a water/acetone mixture as the hemi-hydrate with a melting point of 250°-252° (decomposition).

EXAMPLE 19

Analogously to Example 17, 4-[3-(2-(3,4-methylenedioxyphenyl)-ethylamino)-2-hydroxy-propoxy]-benzimidazol-2-one is obtained from 2.8 g of 4-(2,3-epoxypropoxy)-benzimidazol-2-one and 12.3 g of 2-(3,4-methylenedioxy-phenyl)-ethylamine and is dissolved in acetone and an ethereal solution of hydrogen chloride is added to this solution, whereupon the hydrochloride is obtained; this is recrystallised from methanol/acetone; the salt sinters at 243° and melts at 249°-251°.

What is claimed is:
1. A compound of the formula

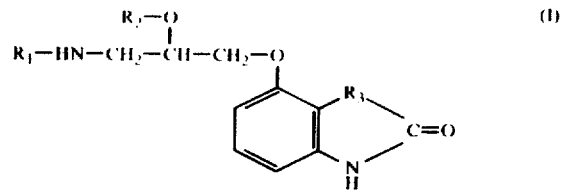

in which $R_1$ denotes optionally substituted lower alkyl which is optionally branched at the linking carbon atom, $R_2$ represents hydrogen or lower alkanoyl and $R_3$ is a group of the formula —O—$CH_2$— or of the formula —$CH_2$—O— in the form of a racemate, optical antipodes or an acid addition salt thereof which can be used pharmaceutically.

2. A compound as claimed in claim 1, in which $R_1$ denotes lower alkyl with 3-5 carbon atoms which is optionally branched at the linking carbon atom and can be substituted, on a carbon atom other than the linking carbon atom, by phenyl which optionally contains hydroxyl, as well as lower alkyl, lower alkoxy, methylenedioxy or halogen, or by phenoxy which optionally contains carbamoyl, $R_2$ represents hydrogen and $R_3$ represents the group of the formula —O—$CH_2$— or of the formula —$CH_2$—O— in the form of a racemate, optical antipodes or an acid addition salt thereof which can be used pharmaceutically.

3. A compound as claimed in claim 1, in which $R_1$ denotes lower alkyl with 3-5 carbon atoms which is optionally branched at the linking carbon atom or denotes 2-phenyl-lower alkyl, in which lower alkyl contains up to 3 carbon atoms, which is optionally substituted in the phenyl part by lower alkoxy or methylenedioxy, $R_2$ represents hydrogen and $R_3$ denotes the group of the formula —O—$CH_2$— or of the formula —$CH_2$—O— in the form of a racemate, optical antipodes or an acid addition salt thereof which can be used pharmaceutically.

4. A compound as claimed in claim 1 which is 8-(3-tert.-butylamino-2-hydroxy-propoxy)-2,3-dihydro-4H-benz[5,6]oxazin-3-one in the form of a racemate, optical antipodes or an acid addition salt thereof which can be used pharmaceutically.

5. A compound as claimed in claim 1 which is 7-(3-tert.-butylamino-2-hydroxy-propoxy)-4H-1,3-benzoxazin-2(1H)-one in the form of a racemate, optical antipodes or an acid addition salt thereof which can be used pharmaceutically.

6. The hydrochloride salt of the compound of claim 4.

7. The hydrochloride salt of the compound of claim 5.

8. A pharmaceutical composition useful in the treatment of disorders in the cardiac rhythm and coronary heart diseases as well as of hypertension comprising a therapeutically effective amount of a compound of formula I as claimed in claim 1, or an acid addition salt thereof which can be used pharmaceutically, together with a pharmaceutically acceptable excipient.

9. A method for the treatment of disorders in the cardiac rhythm and coronary heart diseases as well as of hypertension in a warm-blooded animal which comprises the administration thereto of a therapeutically effective amount of a compound of formula I defined in claim 1.

* * * * *